United States Patent
Maxik et al.

(10) Patent No.: US 9,018,854 B2
(45) Date of Patent: Apr. 28, 2015

(54) LIGHTING SYSTEM WITH REDUCED PHYSIONEURAL COMPRESSION AND ASSOCIATE METHODS

(71) Applicant: Lighting Science Group Corporation, Satellite Beach, FL (US)

(72) Inventors: Fredric S. Maxik, Indialantic, FL (US); David E. Bartine, Cocoa, FL (US); Robert R. Soler, Cocoa Beach, FL (US); Eliza Katar Grove, Satellite Beach, FL (US); Matthew Regan, Melbourne, FL (US)

(73) Assignee: Biological Illumination, LLC, Melbourne, FL (US)

( * ) Notice: Subject to any disclaimer, the term of this patent is extended or adjusted under 35 U.S.C. 154(b) by 55 days.

(21) Appl. No.: 13/830,390

(22) Filed: Mar. 14, 2013

(65) Prior Publication Data

US 2014/0265937 A1    Sep. 18, 2014

(51) Int. Cl.
*H05B 37/02* (2006.01)
*A61M 21/00* (2006.01)
(Continued)

(52) U.S. Cl.
CPC ........... *H05B 37/0281* (2013.01); *A61M 21/00* (2013.01); *H05B 33/0857* (2013.01); *A61M 2021/0044* (2013.01); *A61N 5/0618* (2013.01); *A61N 5/0622* (2013.01); *A61N 2005/0662* (2013.01)

(58) Field of Classification Search
USPC ............................ 362/231; 315/291, 307, 360
See application file for complete search history.

(56) References Cited

U.S. PATENT DOCUMENTS 5,523,878 A    6/1996  Wallace et al.
5,680,230 A    10/1997 Kaburagi et al.
5,704,701 A    1/1998  Kavanagh et al.
(Continued)

FOREIGN PATENT DOCUMENTS

CN    101 702 421 A    5/2010
WO    2008/146220 A2   12/2008
(Continued)

OTHER PUBLICATIONS

International Search Report prepared by the International Searching Authority for related International Application No. PCT/US2014/024459, filed Mar. 12, 2014 (4 pages).
(Continued)

*Primary Examiner* — Thuy Vinh Tran
(74) *Attorney, Agent, or Firm* — Mark R. Malek; Daniel C. Pierron; Widerman Malek, PL (57) ABSTRACT

A system for generating light with reduced physioneural compression. The system includes a first light source operable to emit light within a first wavelength range corresponding to a first photoreceptor and a second light source operable to emit light within a second wavelength range corresponding to a second photoreceptor. The system includes a controller functionally coupled to each of the first light source and the second light source. The controller is configured to alternately operate one of the first light source and the second light source with a duty cycle that is less than a response time of the visual cortex, but greater than a response time of physioneural cells, optionally including a latency between operation of light sources. The system may further include a third light source corresponding to a third photoreceptor.

18 Claims, 8 Drawing Sheets

(51) Int. Cl.
*H05B 33/08* (2006.01)
*A61N 5/06* (2006.01)

(56) References Cited

U.S. PATENT DOCUMENTS

| | | | |
|---|---|---|---|
| 5,997,150 A | 12/1999 | Anderson | |
| 6,140,646 A | 10/2000 | Busta et al. | |
| 6,341,876 B1 | 1/2002 | Moss et al. | |
| 6,356,700 B1 | 3/2002 | Strobl | |
| 6,594,090 B2 | 7/2003 | Kruschwitz et al. | |
| 6,767,111 B1 | 7/2004 | Lai | |
| 6,817,735 B2 | 11/2004 | Shimizu et al. | |
| 6,870,523 B1 | 3/2005 | Ben-David et al. | |
| 6,871,982 B2 | 3/2005 | Holman et al. | |
| 6,974,713 B2 | 12/2005 | Patel et al. | |
| 7,072,096 B2 | 7/2006 | Holman et al. | |
| 7,075,707 B1 | 7/2006 | Rapaport et al. | |
| 7,083,304 B2 | 8/2006 | Rhoads | |
| 7,125,142 B2 * | 10/2006 | Wainwright | 362/231 |
| 7,178,941 B2 | 2/2007 | Roberge et al. | |
| 7,246,923 B2 | 7/2007 | Conner | |
| 7,255,469 B2 | 8/2007 | Wheatley et al. | |
| 7,261,453 B2 | 8/2007 | Morejon et al. | |
| 7,289,090 B2 | 10/2007 | Morgan | |
| 7,300,177 B2 | 11/2007 | Conner | |
| 7,303,291 B2 | 12/2007 | Ikeda et al. | |
| 7,325,956 B2 | 2/2008 | Morejon et al. | |
| 7,342,658 B2 | 3/2008 | Kowarz et al. | |
| 7,349,095 B2 | 3/2008 | Kurosaki | |
| 7,400,439 B2 | 7/2008 | Holman | |
| 7,429,983 B2 | 9/2008 | Islam | |
| 7,434,946 B2 | 10/2008 | Huibers | |
| 7,436,996 B2 | 10/2008 | Ben-Chorin | |
| 7,438,443 B2 | 10/2008 | Tatsuno et al. | |
| 7,476,016 B2 | 1/2009 | Kurihara | |
| 7,520,642 B2 | 4/2009 | Holman et al. | |
| 7,530,708 B2 | 5/2009 | Park | |
| 7,540,616 B2 | 6/2009 | Conner | |
| 7,556,406 B2 | 7/2009 | Petroski et al. | |
| 7,598,686 B2 | 10/2009 | Lys et al. | |
| 7,598,961 B2 | 10/2009 | Higgins | |
| 7,626,755 B2 | 12/2009 | Furuya et al. | |
| 7,677,736 B2 | 3/2010 | Kazasumi et al. | |
| 7,684,007 B2 | 3/2010 | Hull et al. | |
| 7,703,943 B2 | 4/2010 | Li et al. | |
| 7,705,810 B2 | 4/2010 | Choi et al. | |
| 7,709,811 B2 | 5/2010 | Conner | |
| 7,719,766 B2 | 5/2010 | Grasser et al. | |
| 7,728,846 B2 | 6/2010 | Higgins et al. | |
| 7,766,490 B2 | 8/2010 | Harbers et al. | |
| 7,828,453 B2 | 11/2010 | Tran et al. | |
| 7,832,878 B2 | 11/2010 | Brukilacchio et al. | |
| 7,834,867 B2 | 11/2010 | Sprague et al. | |
| 7,845,823 B2 | 12/2010 | Mueller et al. | |
| 8,016,443 B2 | 9/2011 | Falicoff et al. | |
| 8,047,660 B2 | 11/2011 | Penn et al. | |
| 8,049,763 B2 | 11/2011 | Kwak et al. | |
| 8,083,364 B2 | 12/2011 | Allen | |
| 8,083,378 B2 * | 12/2011 | Kiser | 362/293 |
| 8,096,668 B2 | 1/2012 | Abu-Ageel | |
| 8,212,836 B2 | 7/2012 | Matsumoto et al. | |
| 8,297,783 B2 | 10/2012 | Kim | |
| 8,331,099 B2 | 12/2012 | Geissler et al. | |
| 8,337,029 B2 | 12/2012 | Li | |
| 8,378,574 B2 * | 2/2013 | Schlangen et al. | 315/50 |
| 8,556,457 B2 * | 10/2013 | Kiser | 362/231 |
| 8,581,520 B1 * | 11/2013 | Wray | 315/307 |
| 8,742,695 B2 * | 6/2014 | Wray | 315/307 |
| 2004/0052076 A1 | 3/2004 | Mueller et al. | |
| 2006/0002108 A1 | 1/2006 | Ouderkirk et al. | |
| 2006/0002110 A1 | 1/2006 | Dowling et al. | |
| 2006/0164005 A1 | 7/2006 | Sun | |
| 2006/0285193 A1 | 12/2006 | Kimura et al. | |
| 2007/0013871 A1 | 1/2007 | Marshall et al. | |
| 2007/0159492 A1 | 7/2007 | Lo et al. | |
| 2008/0143973 A1 | 6/2008 | Wu | |
| 2008/0198572 A1 | 8/2008 | Medendorp | |
| 2008/0232084 A1 | 9/2008 | Kon | |
| 2009/0059585 A1 | 3/2009 | Chen et al. | |
| 2009/0128781 A1 | 5/2009 | Li | |
| 2010/0006762 A1 | 1/2010 | Yoshida et al. | |
| 2010/0202129 A1 | 8/2010 | Abu-Ageel | |
| 2010/0231863 A1 | 9/2010 | Hikmet et al. | |
| 2010/0244700 A1 | 9/2010 | Chong et al. | |
| 2010/0315320 A1 | 12/2010 | Yoshida | |
| 2010/0320928 A1 | 12/2010 | Kaihotsu et al. | |
| 2010/0321641 A1 | 12/2010 | Van Der Lubbe | |
| 2011/0310446 A1 | 12/2011 | Komatsu | |
| 2012/0286700 A1 | 11/2012 | Maxik et al. | |

FOREIGN PATENT DOCUMENTS

| | | |
|---|---|---|
| WO | 2009/023968 A1 | 2/2009 |
| WO | WO 2009121539 A1 | 10/2009 |
| WO | 2010/122446 A1 | 10/2010 |
| WO | 2011/141842 A1 | 11/2011 |
| WO | WO 2012158665 | 11/2012 |

OTHER PUBLICATIONS

Written Opinion of the International Searching Authority prepared by the International Preliminary Examining Authority for related International Application No. PCT/US2014/024459, filed Mar. 12, 2014 (5 pages).

* cited by examiner

LIGHTING SYSTEM WITH REDUCED PHYSIONEURAL COMPRESSION AND ASSOCIATE METHODS

FIELD OF THE INVENTION

The present invention relates to systems and methods for providing light with reduced physioneural compression.

BACKGROUND OF THE INVENTION

The total amount of light emitted by a light source, or radiant flux, is never fully perceived by an observer results in a difference between the actual brightness of light being emitted and a perceived brightness. The reduced perceived brightness is due to a number of factors. First, the human eye has varying levels of sensitivity depending on the wavelength (s) of light that are perceived. However, another reason for reduced perceived brightness is a biological phenomenon referred to as physioneural compression.

The eye of an observer comprises thousands of photoreceptor cells, including rod cells and cone cells. Furthermore, there are three types of cone cells, namely long, medium, and short. Each type of cone cells is more responsive to different ranges of wavelengths of light. Long cone cells have a peak responsiveness around 564-580 nanometers, medium cone cells around 534-545 nanometers, and short cone cells around 420-440 nanometers. Physioneural compression occurs when light is incident upon the cone cells and includes two or more wavelengths of light that generate responses in two or more types of cone cells. When this occurs, physioneural cells, which are in communication with the cone cells, are forced to integrate the visual information into a signal to be transmitted to the visual cortex of the brain, which then further interprets the visual information and causes the observer to have a coherent understanding of the visual information. When physioneural cells interpret information from more than one type of cone cell at a time, it reduces the perceived brightness of the sum of the visual information received.

For example, if long cone cells are providing visual information with a normalized brightness of one unit, and short cone cells are also providing visual information with a normalized brightness of one unit, the physioneural cells transmit that visual information to the visual cortex with a brightness of less than one unit. This is how present lighting devices operate. Accordingly, there is a need for a lighting device that emits light in such a way as to avoid physioneural compression, thereby increasing the perceived brightness of the light.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the foregoing in mind, embodiments of the present invention are related to a system for generating light with reduced physioneural compression. The system may include a first light source operable to emit light within a first wavelength range corresponding to a first color and a second light source operable to emit light within a second wavelength range corresponding to a second color. The system may further include a controller functionally coupled to each of the first light source and the second light source. The first color may be a color opponent of the second color. Additionally, the controller may be configured to alternately operate one of the first light source and the second light source. Furthermore, the controller may be configured to alternately operate each of the first and second light sources with a duty cycle that is less than a response time of a visual cortex of an observer, but greater than a response time of physioneural cells of the observer. Physioneural cells may be any physiological element that is associated with or in any way facilitates the perception, transmission, or conversion of visual information between photodetector cells and substances and the visual cortex of the brain. Additionally, the emission sequence of the light sources may be altered so as to alter the perceived brightness of the light.

Another embodiment of the present invention is related to a system for generating light with reduced physioneural compression including a first light source configured to emit light that generates a response primarily in long cone cells, a second light source configured to emit light that generates a response primarily in medium cone cells, and a third light source configured to emit light that generates a response primarily in short cone cells. The system may further include a controller functionally coupled to each of the first light source, the second light source, and the third light source. The controller may be configured to alternately operate a combination of at least two of the first light source, the second light source, and the third light source with a duty cycle that is less than a response time of a visual cortex of an observer, but greater than a response time of physioneural cells of the observer.

Another embodiment of the present inventions is directed to a method of emitting light having reduced physioneural compression using a lighting system comprising a first light source configured to emit light that generates a response primarily in long cone cells, a second light source configured to emit light that generates a response primarily in medium cone cells, a third light source configured to emit light that generates a response primarily in short cone cells, and a controller functionally coupled to each of the first light source, the second light source, and the third light source. The method may include the step of first operating one of the first light source, the second light source, and the third light source for a first period. The method may continue with the step of operating one of the first light source, the second light source, and the third light source that is a color opponent of the light source operated during the first period for a second period. The time elapsed during the sum of the first period and the second period is less than the response time of the visual cortex. Furthermore, the time elapsed during each of the first period and the second period is greater than the response time of physioneural cells.

DETAILED DESCRIPTION OF THE PREFERRED EMBODIMENT

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, a person skilled in the art should note that references to lighting systems, such as "lamp," "luminaire," "bulb," and other like terms are used for the convenience of the reader in reference to the drawings. Any system that generates light is included within the scope of the present invention.

An embodiment of the invention, as shown and described by the various figures and accompanying text, provides a lighting system the emits light that is configured to reduce the reduction of perceived brightness of light emitted by the lighting system by physioneural compression of the physioneural cells of an observer of the light. The lighting system reduces the physioneural compression by alternately emitting light having a wavelength range that corresponds to the range of wavelengths a photoreceptor cells responds to. More specifically, the lighting system may be configured to alternately emit light having wavelength ranges that correspond to responsive wavelength ranges of cone cells, such as long cone cells, medium cone cells, and short cone cells. In some embodiments, the lighting system may be configured to emit light having wavelength ranges that correspond to responsive wavelength ranges of other photoreceptor cells, such as rod cells, as well as other physiological elements that are involved with the perception of light, including melanopsin. Moreover, some individuals have been identified as having a fourth type of cone cell, and hence having tetrachromatic vision. The lighting system may be configured to emit light within a wavelength range to which any of the aforementioned physiological elements may be responsive to, as well as any future discovered physiological elements. Moreover, the lighting system may alternate emitting light within the wavelength ranges wherein the light-emitting elements have a duty of cycle of less than a response time of the visual cortex of the observer, but greater than a response time of the physioneural cells.

Figure 1:
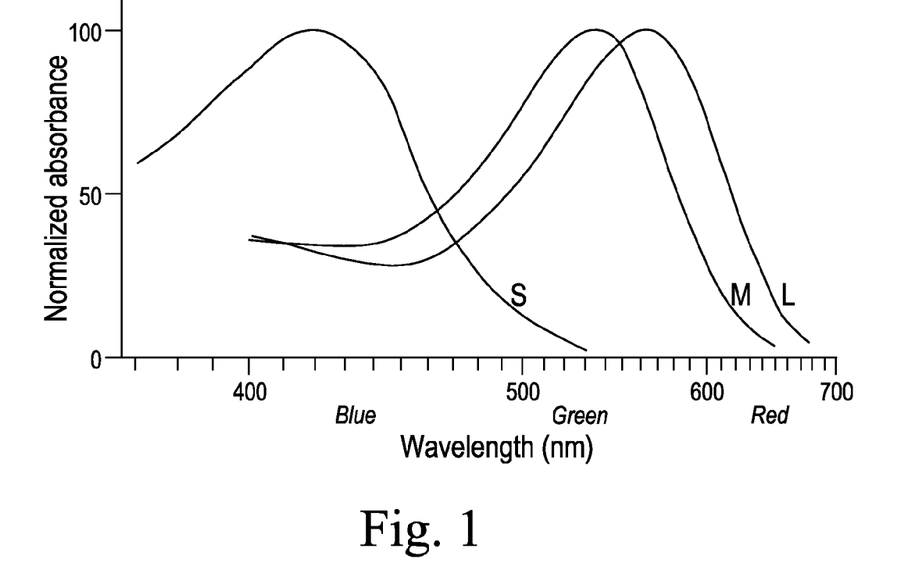
FIG. 1 illustrates the normalized responsivity spectral of human cone cells.

Referring now to FIG. 1, a graph of approximate photoreceptor absorbance of wavelengths of light is presented. As can be seen in the graph, S cone cells, or small cone cells, have a peak absorbancy at about 420 nanometers, corresponding to a generally blue-colored light. M cone cells, or medium cone cells, have a peak absorbancy at about 534 nanometers, corresponding to a generally green-colored light. L cone cells, or long cone cells, have a peak absorbancy at about 564 nanometers, corresponding to a generally red-colored light. As described above, physioneural compression occurs when the physioneural cells (PCs) of the retina of an eye of an observer of a light perceives light that two or more type of cone cells are responsive to and absorb. When a PC receives visual information from the two or more types of cone cells, the PC simultaneously interprets the visual information from the cone cells to determine the perceived color while also compressing the brightness of light perceived individually by each of the two types of cone cells. The compression of brightness causes the PC to transmit visual information to the visual cortex of the brain with a perceived color and a perceived brightness, the perceived brightness being less than the sum of the brightnesses perceived by each of the two types of cone cells individually.

Figure 3:
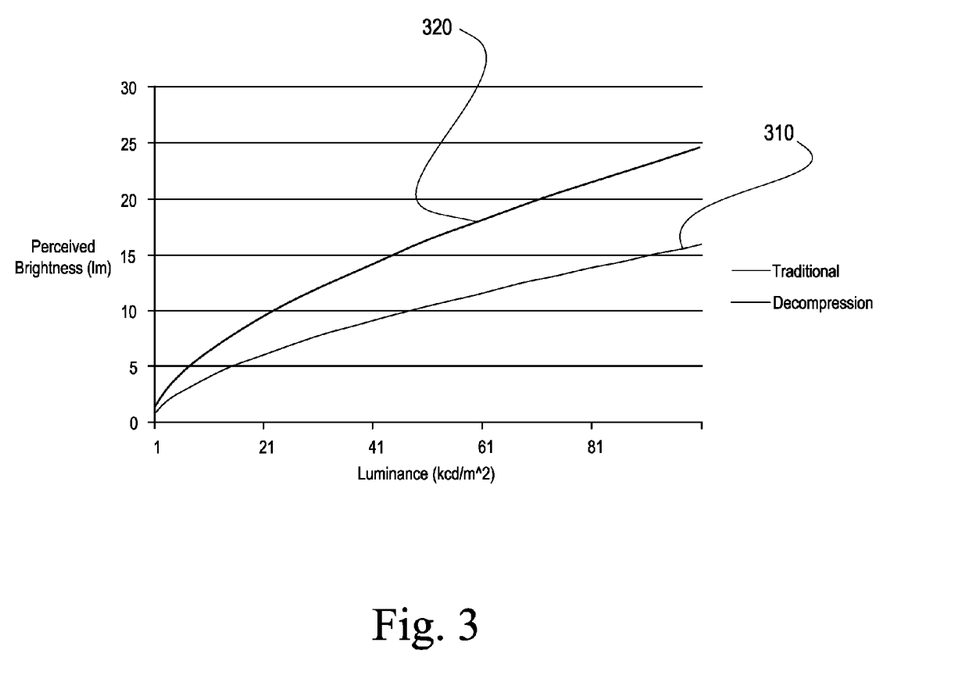
FIG. 3 illustrates perceived brightness of traditional lighting systems versus the perceived brightness of the invention.

Referring now to FIG. 3, the perceived brightness of a polychromatic light that the simultaneously includes wavelengths of light that are primarily absorbed by two or more types of cone cells may be approximated by the equation:

$$B = L^{0.6},$$

which is represented by plot 310. In contrast, a perceived brightness of a lighting system according to the present invention may be approximated by the equation:

$$B = 3\left(\left(\frac{1}{3}\right)^{.6} L^{0.6}\right)$$

which is represented by plot 320. The perceived brightness of plot 320 represents how a lighting system according to the prevent invention may achieve the same perceived brightness of a traditional lighting system represented in plot 310 with significantly lower luminance, which results in reduced power consumption by the light emitting element of the lighting system. Additionally, such an increase in perceived brightness may allow a lighting system to include fewer light emitting elements, reducing the material cost in fabricating such a lighting system. Moreover, in systems where the efficiency of the light emitting element is reduced by an increase in temperature, a lighting system according to the present invention may generally produce less heat than a traditional lighting system, further increasing the electrical efficiency of the system. Furthermore, reducing the temperature of the light emitting element of the lighting system may increase the longevity of the light emitting element.

Accordingly, a lighting system according to the present invention may include one or more light sources that are configured to emit generally monochromatic light that is configured to be absorbed primarily by a single type of cone cell and generally not be absorbed, or be absorbed only at a very low rate, by the other types of cone cells. Moreover, the lighting system may be configured to emit an instantaneous light that includes light within a wavelength range corresponding to an absorption range associated with a single type of cone cell. The lighting system may further be configured to emit a sequence of instantaneous lights, wherein each instantaneous light in the sequence is within a wavelength range corresponding to an absorption range associated with a single type of cone cell, but the type of cone cell associated with the light varies among the instantaneous lights in the sequence. Furthermore, the duration of the instantaneous light may be such that it may be discriminately perceived by the PCs, which is to say that the duration is greater than a response time of the PCs. Moreover, the duration of the instantaneous light may be such that it is indiscriminately perceived by the visual cortex, resulting in the visual cortex blending the color of successive instantaneous lights of the sequence. This is to say that the duration is less than a response time of the visual cortex.

Figure 2:
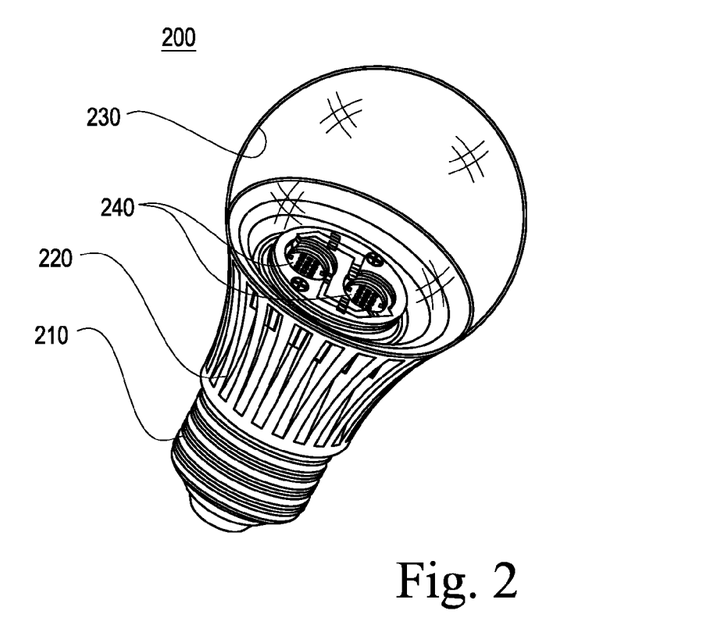
FIG. 2 is a perspective view of a lamp according to an embodiment of the invention.

Referring now to FIG. 2, a lighting system according to an embodiment of the invention is presented. In the present embodiment, the lighting system may include a lamp 200. The lamp 200 may be configured to generally comply with the geometry of a light bulb standard. The lamp 200 may include a base 210, a heat sink 220, and an optic 230. As will be described below, the lamp 200 may include one or more light sources 240 and associated circuitry configured to produce light having reduced physioneural compression.

The base 210 may be any type of bulb fitting known in the art, including, but not limited to, Edison, bayonet, bi-post, bi-pin, and wedge fittings. Additionally, the base 210 may be configured to conform to the various sizes and configurations of the aforementioned fittings. The base 210 may be formed of an electrically conductive material such as aluminum. In alternative embodiments, the base 210 may be formed of other electrically conductive materials such as silver, copper, gold, conductive alloys, and the like. Internal electrical leads (not shown) may be attached to the base 210 to serve as contacts for a light socket (not shown).

The heat sink 220 may be configured to increase the heat dissipation capacity of the lamp 200. Accordingly, the heat sink 220 may be positioned in thermal communication with any heat-generating element of the lamp 200, such as the light sources 240 and associated circuitry. Furthermore, the heat sink 220 may be configured to be shaped and include features that increase its heat-dissipating capacity. In some embodiments, the heat sink 220 may include a plurality of fins 222 serving to increase the surface area of the heat sink. Moreover, the heat sink 220 may be formed of any thermally conductive material such as aluminum, copper, steel, thermally-conductive polymers, and the like.

The optic 230 may be configured to define an optical chamber such that light emitted by the light sources 240 will enter the optical chamber. The optic 230 may be positioned such that light emitted by the light sources 240 traverses the optical chamber and is transmitted through the optic 230 into the environment surrounding the lamp 200. The optic 230 may be formed into any shape or configuration. Moreover, the optic 230 may be shaped to conform to a standardized shape for a light bulb. Additionally, the optic 230 may be configured to be optically transparent or translucent. In some embodiments, the optic 230 may be configured to operate as an optic diffusing element by incorporating diffusing technology, such as described in U.S. Pat. No. 7,319,293 titled Light Bulb Having Wide Angle Light Dispersion Using Crystalline Material filed Aug. 9, 2004, the content of which is incorporated herein in its entirety by reference. Furthermore, in some other embodiments, the optic 230 may be formed of a light diffusive plastic or polymer, may include a light diffusive coating, or may have diffusive particles attached to or embedded therein.

The light sources 240 may be any device configured to emit light. The light sources 240 may include one or more light emitting elements. The light emitting elements may be any device capable of emitting light, including light emitting semiconductors, incandescent bulbs, halogen lamps, gas-discharge lamps, and fluorescent lamps. In the present embodiment, the light emitting elements may be light emitting semiconductors, or, more specifically, light emitting diodes (LEDs).

Figure 4:
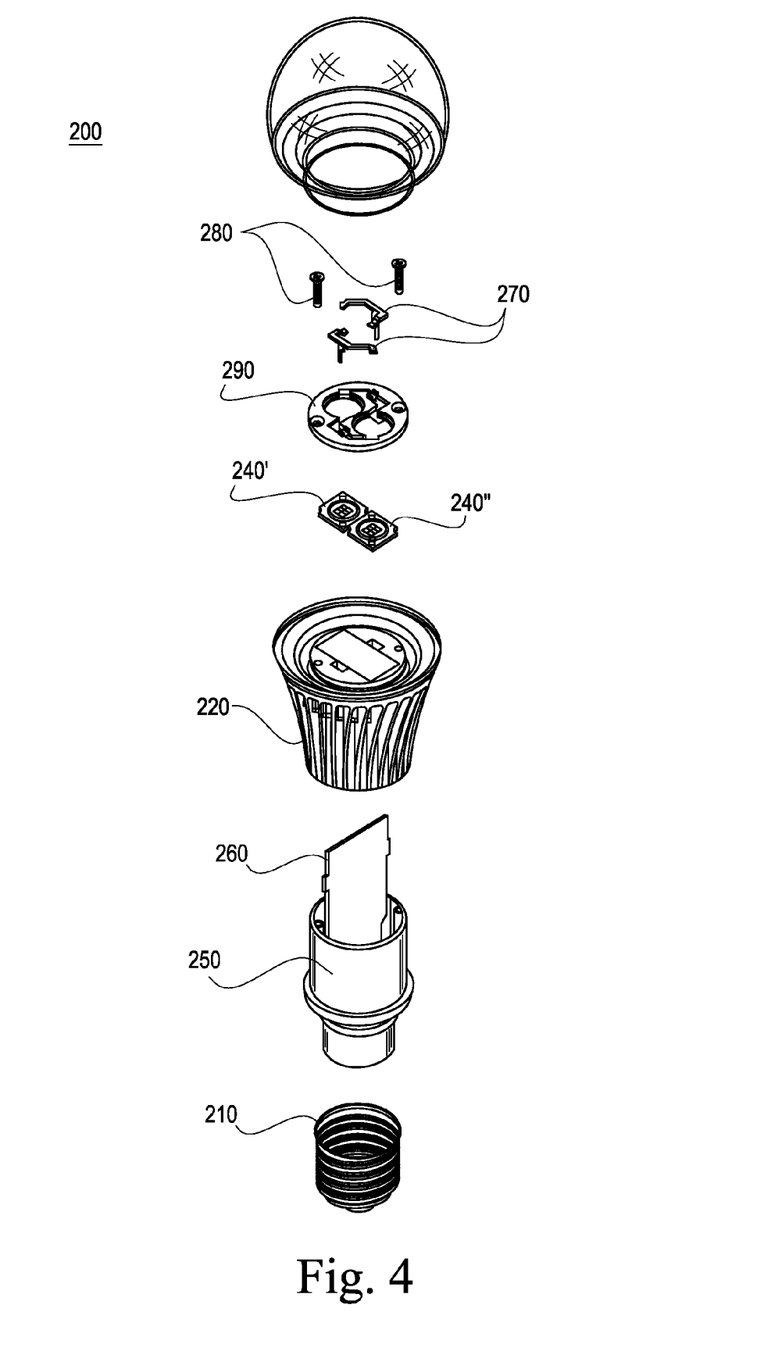
FIG. 4 is an exploded perspective view of the lamp of FIG. 2.

Turning now to FIG. 4, an exploded view of the lamp 200, illustrating internal components of the lamp 200, is presented. As shown, in addition to the components described above, the lamp 200 may also include a housing 250, a printed circuit board (PCB) 260, spring wire connectors 270, screws 280, and a holder 290.

The PCB 260 may include dedicated circuitry to power, drive, and control one or more of the light sources 240. The PCB 260 may include a driver circuit and a power circuit. The circuitry on the PCB 260 may serve as a means for powering and driving the light sources 240. In one embodiment, the driver circuit may be configured to include a controller that is functionally coupled to each of the light sources 240. In one embodiment, the controller may be functionally coupled to a first light source 240' and a second light source 240". The controller may be configured to operate each of the first light source 240' and the second light source 240" to have a duty cycle during which the light source 240 emits light. Furthermore, the controller may be configured to operate each of the first light source 240' and the second light source 240" having a duty cycle that reduces physioneural compression.

Figure 5:
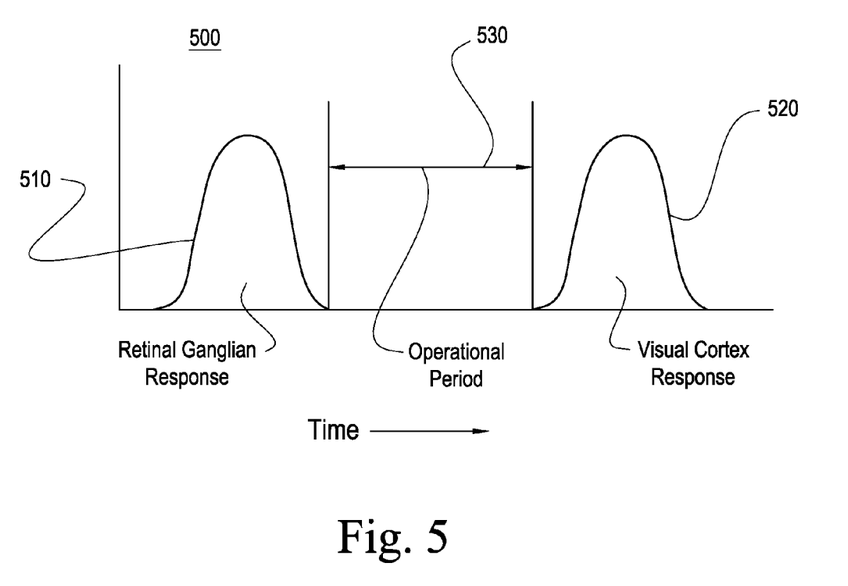
FIG. 5 illustrates an operational period range for an embodiment of the invention.

Referring now to FIG. 5, a graph 500 illustrating an operational period of a lighting system according to an embodiment of the invention is depicted. A first plot 510 of the graph 500 is an approximate distribution of PC response times for humans. PC response time may be generally considered to be less than about 2 milliseconds. A second plot 520 of the graph 500 is an approximate distribution of visual cortex response times for humans. Visual cortex response time may be generally considered to be at least about 20 milliseconds. There is a region of the graph 500 between each of the first plot 510 and the second plot 520 that represents a gap between each of the respective response times. This gap is illustrated by element 530 and defines an operational period range of a lighting system according to an embodiment of the invention. The operational period range may be from about 2 milliseconds to about 20 milliseconds. In some embodiments, the operational period may be about 20 milliseconds, about 16.67 milliseconds, about 10 millisecond, about 8.33 milliseconds, about 6.67 milliseconds, about 5.56 milliseconds, about 5 milliseconds, about 4.17 milliseconds, about 3.33 milliseconds, or about 2.22 milliseconds.

A light source that emits a first light for a length of time that falls within the operational period range 530 will be discretely perceived by PCs and transmitted to the visual cortex. The first light may be a light having a wavelength range that corresponds to a wavelength range that a photoreceptor cell of a human, such as, for example, a cone cell, will respond to. Furthermore, a light source that emits a subsequent second light for a length of time that similarly falls within the operational period range 530 will also be discretely perceived by PCs. Similarly, the second light may be a light having a wavelength range that corresponds to a wavelength range that a photoreceptor cell of a human, such as a cone cell, will respond to. The particular type of photoreceptor cell that responds to the second light may be different than the type of photoreceptor cell that responds to the first light, as described hereinabove.

When the first light and the second light are emitted in sufficiently rapid succession, in spite of each light being discretely perceived and transmitted by PCs, the visual cortex will perceive the lights in a combined fashion, perceiving the lights as a combined light. The characteristics of the combined light may be such that the wavelengths of each of the first light and the second light, each corresponding to a color, may be combined to form a functional equivalent of a metamer, the metamer having an apparent color that is approximately a blend, combination, or average of the colors of each of the first and second lights. In contrast, the brightness of the combined light will not be compressed by PCs, as only a single type of photoreceptor cell will be active at a given time. Accordingly, the perceived brightness of the combined light may be approximated by plot 320 of FIG. 3, representing an increase in perceived brightness over a lighting system where the first light and the second light are emitted concurrently, as approximated by plot 310.

Referring now back to FIG. 4, the controller of the driver circuit of the PCB 260 may be configured to operate the light sources 240 to have a duty cycle that is within the operational period range 530 as represented in FIG. 5. More specifically, the controller may be configured to operate the first light source 240' with a duty cycle that is within the operational period range 530. Moreover, the first light source 240' may be configured to emit light having a wavelength range that corresponds to a wavelength range that a photoreceptor cell may respond to. For example, the first light source 240' may emit a light having a wavelength range corresponding to a generally green light. Accordingly, medium cone cells of an observer may respond to the light emitted by the first light source 240'. Furthermore, the second light source 240" may emit a light having a wavelength range corresponding to a generally blue light source. Accordingly, small cone cells of an observer may respond to the light emitted by the second light source 240".

It is contemplated and within the scope of the invention that each of the first light source 240' and the second light source 240" may emit light having a wavelength range corresponding to any color of the visible spectrum. In some embodiments, the light sources 240 may be configured to emit monochromatic light. In some further embodiments, the light sources 240 may be configured to emit monochromatic light corresponding to wavelength ranges that a photoreceptor cell may respond to. In some further embodiments, the light sources 240 may be configured to emit polychromatic light. Moreover, the light sources 240 may be configured to emit polychromatic light including a constituent light having a wavelength range corresponding to wavelength ranges that a photoreceptor cell may respond to. Moreover, the controller may be functionally coupled to light sources 240 configured to emit polychromatic light such that the controller may selectively operate the light sources 240 to emit light having a wavelength range corresponding to a wavelength range that a photoreceptor cell may respond to. Furthermore, it is contemplated that the lamp 200 may include any number of light sources 240, and the depiction of the lamp 200 including two light sources 240', 240" is exemplary only and does not limit the scope of the invention. For example, and not by means of limitation, the lamp 200 may include a third light source (not shown), wherein the first light source 240' is configured to emit monochromatic light having a wavelength range, such as a wavelength range corresponding to generally red light, corresponding to a wavelength range to which a first photoreceptor cell, such as a long-type cone cell, may be responsive to. Furthermore, the second light source 240" may be configured to emit monochromatic light having a wavelength range, such as a wavelength range corresponding to generally green light, corresponding to a wavelength range to which a second photoreceptor cell, such as a medium-type cone cell, may be responsive to. Yet further, the third light source may be configured to emit monochromatic light having a wavelength range, such as a wavelength range corresponding to a generally blue light, corresponding to a wavelength range to which a third photoreceptor cell, such as a short-type cone cell, may be responsive to. The controller may be functionally coupled to each of the first light source 240', the second light source 240", and the third light source so as to alternately operate each of the light sources 240 with a duty cycle within the operational period range 530.

Furthermore, in some embodiments, the controller may be configured to selectively operate the light sources 240 to alter, manipulate, or otherwise change the characteristic of light emitted by each of the light sources 240, and hence by the lamp 200. For example, in some embodiments, the controller may alter the average luminous intensity of light emitted by the light sources 240 so as to alter the perceived brightness of light emitted by the lamp 200. For example, the controller may employ pulse width modulation (PWM) to generally reduce the luminous intensity of light emitted by the light sources 240 to reduce the luminous intensity from a maximum luminous intensity, thereby reducing the perceived brightness of the light emitted by the lamp 200. Furthermore, the lamp may vary the duty cycle of the various light sources 240 such that a light source 240 of a certain color may be greater than the duty cycle of another light source 240 of a different color, thereby affecting the perceived color of the light emitted by the lamp 200. Furthermore, in some embodiments, the light sources 240 may be configured to emit a generally white light when operated according to a first proportion of duty cycles for each of the light sources 240, and may include a red light source and a blue light source. The white light may have associated with it a color temperature. The controller may be configured to generally reduce the color temperature of the white light by increasing the duty cycle of the red light source relative to the duty cycle of the other light sources 240. Furthermore, the controller may be configured to increase the color temperature of the white light by increasing the duty cycle of the blue light source relative to the duty cycle of the other light sources 240. In one embodiment, the first proportion of duty cycles may generate a white light having a color temperature of about 6000 Kelvin. In other embodiments, the first proportion of duty cycles may generate a white light having a color temperature of about 2000 Kelvin, about 2500 Kelvin, about 2700 Kelvin, about 2800 Kelvin, about 2900 Kelvin, about 3000 Kelvin, about 3100 Kelvin, about 3200 Kelvin, about 3300 Kelvin, about 3350 Kelvin, about 3500 Kelvin, about 4000 Kelvin, about 4500 Kelvin, about 5000 Kelvin, or about 5500 Kelvin.

Continuing to refer to FIG. 4, the PCB 260 may be configured to be positioned at least partially within and carried by each of the housing 250 and the heat sink 220. Furthermore, the housing 250 may be configured to be positioned at least partially within and carried by each of the base 210 and the heat sink 220. The heat sink 220 may be configured to facilitate the positioning of the light sources 240 thereupon. Furthermore, the holder 290 may be configured to cooperate with the heat sink 220 to secure the light sources 240, preventing movement of the light sources 240 relative to the other elements of the lamp 200. Each of the heat sink 220 and the holder 290 may be configured to cooperate with the screws 280 to further facilitate the securing of the light sources 240. It is contemplated that any securing device, including fasteners, welding, adhesives, and the likes, may be used in securing the light sources 240, and each of the heat sink 220 and the holder 290 may be configured to cooperate therewith. The spring wire connectors 270 may be configured to place the light sources 240 in electrical communication with the PCB 260 and its constituent elements. The spring wire connectors 270 may be configured to facilitate electrical connection between the circuitry of the PCB 260 and the light sources 240.

In other embodiments of the invention, the method of emitting light to which certain types of photoreceptor cells respond to may be applied to lighting devices other than lamps, luminaires, or other conventional lighting devices. In some embodiments, a device that is configured to emit light having varying colors may be configured to emit light having reduced PC compression. Such devices may include, without limitation, displays, such as computerized device displays, display adaptors, projectors, and any other device that is capable of emitting light. More specifically, devices that rely on emitting light to convey information across a visible medium are included within the scope of the invention. Additionally, the invention may be employed by a device that relies on backlighting, edge lighting, or any other supplemental light source to increase the brightness of the device, so long as the device is capable of emitting light having a color that one type of photoreceptor cell is responsive to.

Figure 6:
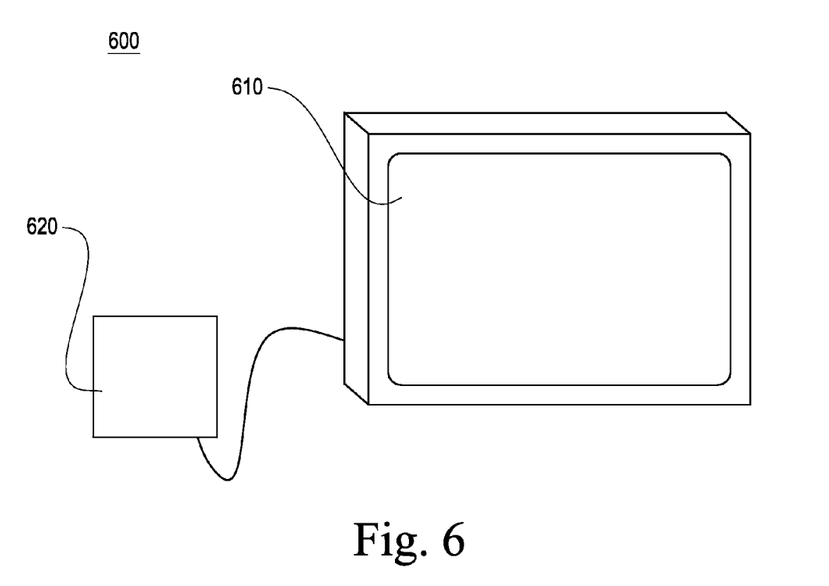
FIG. 6 illustrates an embodiment of the invention comprising a display device.

Referring now to FIG. 6, a depiction of the embodiment described above is presented. In FIG. 6, a display device 600 having a visual display 610 is depicted. The visual display 610 may be any type of display device for conveying information in a visual mode known in the art, including, but not limited to, liquid crystal displays, light-emitting diode displays, organic light-emitting diode displays, cathode ray tube displays, electroluminescent displays, surface-conduction electron-emitter displays, interferometric modular displays, quantum dot displays, carbon nanotube displays, laser displays, digital micromirror device displays, plasma displays, and any other type of display known in the art. For purposes of explanation only, and not by means of limitation, the visual display 610 may be a liquid crystal display comprising a plurality of pixels, each pixel being capable of emitting light within a wavelength range corresponding to a wavelength range a photoreceptor cell is responsive to. Additionally, each pixel may be capable of emitting light and terminate emitting light within the operational range demonstrate by element 530 in FIG. 5.

The display device 600 may further include a display device adaptor 620 configured to control the operation of the visual display 610. In the present embodiment, the display device adaptor 620 is depicted as being separate and apart from the visual display 610 and electrically connected thereto. It is appreciated that in some embodiments the visual display 610 and the display device adaptor 620 may be integrated into a single structural element.

The display device adaptor 620 may be in communication with and able to selectively operate each of the pixels of the visual display 610. When an image, video, or other visual information is received by the display device adaptor 620, the display device adaptor 620 may determine which parts of the received visual information may be subject to physioneural compression, such as colors that are color opponents. The display adaptor may then operate the related plurality of pixels of the visual display 610 to emit a sequence of two or more lights having a wavelength associated with a responsive wavelength range of two or more photoreceptor cells, as described hereinabove and hereinbelow. As such, the visual information depicted by the light emitted by the visual display 610 will accurately represent the information received by the display device adaptor 620 while not having a reduced perceived brightness due to physioneural compression.

Figure 7:
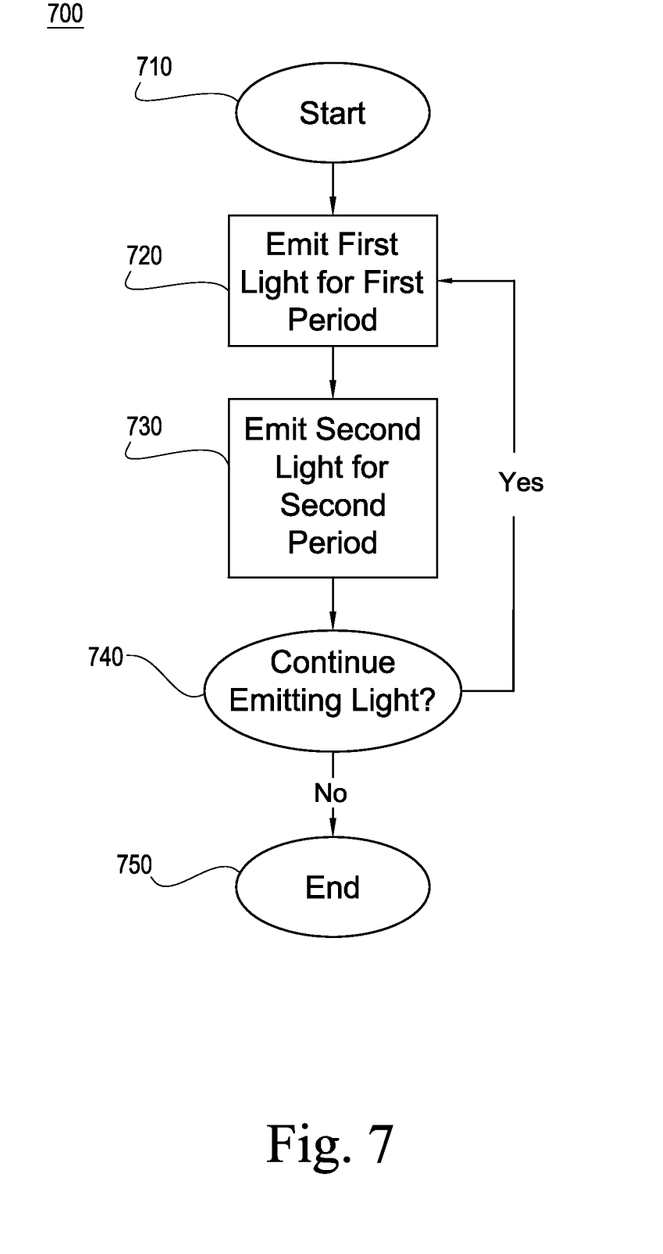
FIG. 7 is a flowchart illustrating a method of emitting light having reduced physioneural compression according to an embodiment of the invention.

Referring now to FIG. 7, a flowchart illustrating a method of operating a lighting device to emit light that reduces physioneural compression is presented. The method 700 illustrates a method of operating a lighting device to emit light to have a perceived brightness as shown by plot 320 in FIG. 3. The method begins at Block 710. At Block 720, the lighting device may emit a first light for a first period. The first light may be operated for a first period of time to have a duty cycle corresponding to the operational period range as described by element 530 in FIG. 5. That is to say, the first light may emit light for a period of time longer than the response time of physioneural cells, but shorter than the response time of a visual cortex. Moreover, the first light may emit a monochromatic light having a wavelength range within a range of wavelengths corresponding to a wavelength range a photoreceptor cell may respond to.

The method may continue at Block 730, where the lighting device may emit a second light for a second period. Similarly, the second period may be a length of time corresponding to the operational period range. Furthermore, the second light may emit a monochromatic light having a wavelength range within a range of wavelengths corresponding to a wavelength range a photoreceptor cell may respond to. In some embodiments, the second light may cause a response in a type of photoreceptor cell that is different from the type of photoreceptor cell that responds to the first light.

At Block 740, the lighting device may determine whether to continue to emit light. This determination may be performed by the circuitry, which may include a controller, as described for the lamp 200 hereinabove. The determination may be made based upon the continued reception of electrical power to the lighting device by an external power source. In other embodiments, the determination may be made based upon a communication received by the lighting device. In such embodiments, the lighting device may include communication circuitry necessary to accomplish such communication, such as that described in U.S. patent application Ser. No. 13/463,020 titled "Wireless Pairing System and Associated Methods" filed May 3, 2012, the content of which is incorporated herein in its entirety by reference. If it is determined that the lighting device will continue emitting light, then the method may return to Block 720. If it is determined the lighting device will not continue emitting light, the method may end at Block 750.

Figure 8:
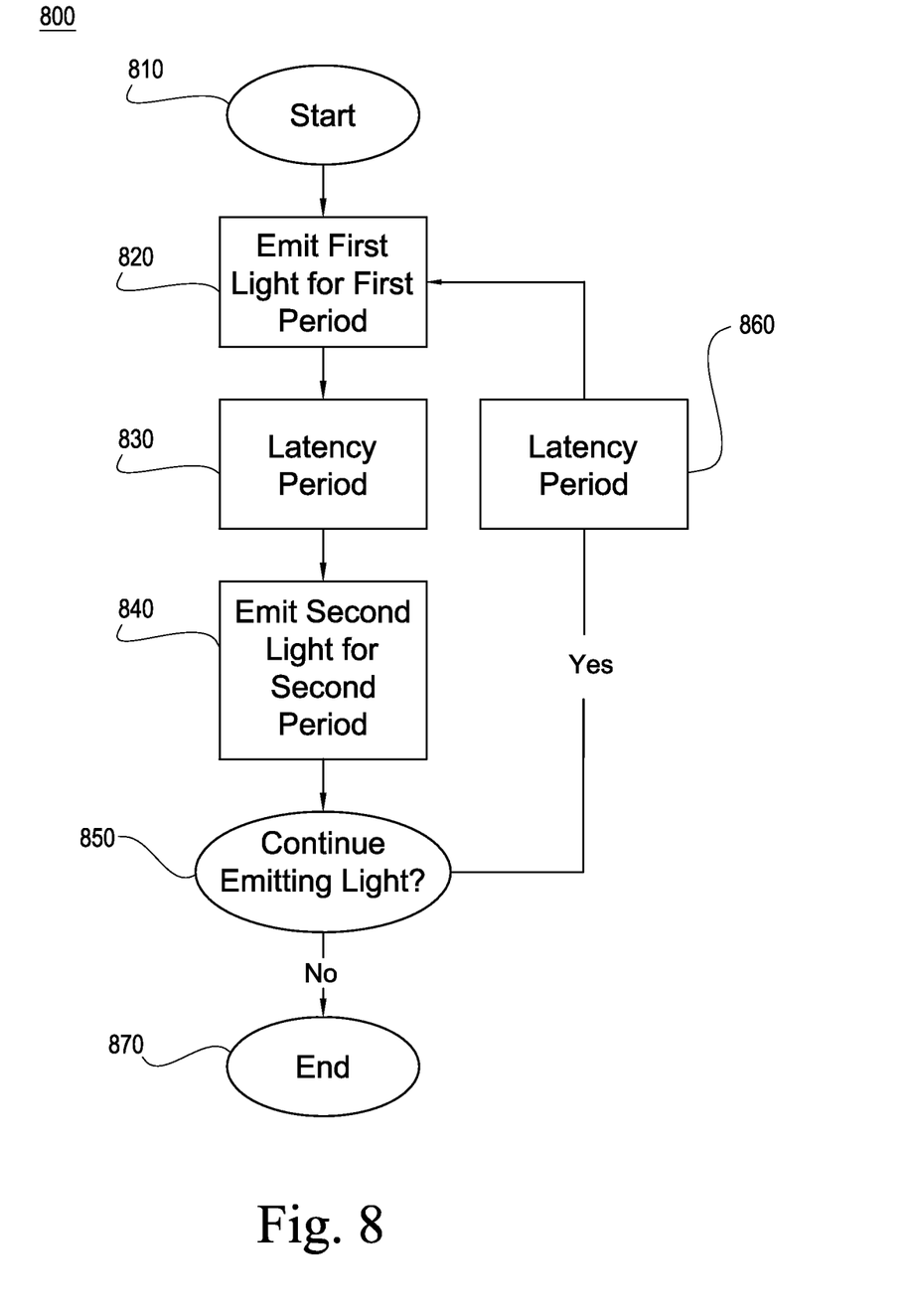
FIG. 8 is a flowchart illustrating a method of emitting light according to the embodiment of FIG. 7 further including a latency period.

Referring now to FIG. 8, a flowchart illustrating a method 800 of operating a lighting device to emit light that reduces physioneural compression similar to the method presented in FIG. 7 is presented. In the method 800 of FIG. 8, a lighting system may be configured to include a latency period between the sequential emissions of light from light sources. The lighting system may be a lighting device as described hereinabove. The latency period may be characterized as a period during which none of the light sources of the lighting system are operated to emit light. An object of including such a latency period is to permit an PC of an observer of light emitted by the lighting system to cease transmitting to the visual cortex light information related to the light previously emitted by the lighting system. Once a period of time has elapsed that corresponds to an approximate discharge time of PCs, a period of time the latency period may be configured to be approximately equal to, the lighting device may operate a light source to emit a subsequent light. The discharge time of PCs may be generally considered to be about 50 nanoseconds.

The method 800 may start at Block 810. At Block 820, the lighting device may emit a first light for a first period. The first light may be operated for a first period of time to have a duty cycle corresponding to the operational period range as described hereinabove. At Block 830, the lighting device may then enter a latency period during which the lighting device does not operate any light source of the lighting device, causing the lighting device to emit no light. The method may continue at Block 840, wherein the lighting device may emit a second light for a second period. Similarly, the second period may be a length of time corresponding to the operational period range. Furthermore, the second light may emit a monochromatic light having a wavelength range within a range of wavelengths corresponding to a wavelength range a photoreceptor cell may respond to. In some embodiments, the second light may cause a response in a type of photoreceptor cell that is different from the type of photoreceptor cell that responds to the first light.

At Block 850, the lighting device may determine whether to continue to emit light. This determination may be performed by the circuitry, which may include a controller, as described for the lamp 200 hereinabove. If it is determined that the lighting device will continue emitting light, then the method may continue at Block 860, where the lighting device may enter another latency period. The latency period of Block 860 may be approximately equal to the latency period of Block 830. The method may then return to Block 820. If, however, it is determined at Block 850 the lighting device will not continue emitting light, the method may end at Block 870.

Figure 9:
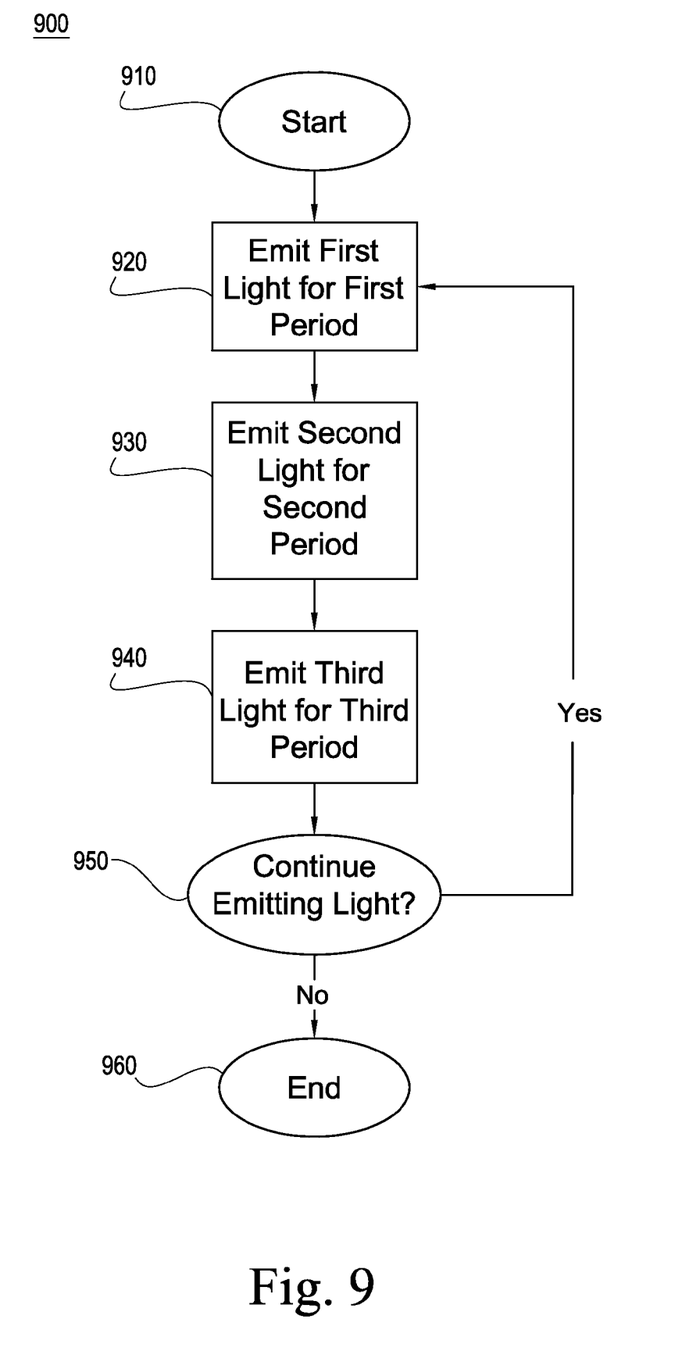
FIG. 9 is a flowchart illustrating a method of emitting light having reduced physioneural compression according to another embodiment of the invention.

Referring now to FIG. 9, a flowchart illustrating a method 900 of operating a lighting device to emit light that reduces physioneural compression is presented. In the present embodiment, a lighting system may be a lighting device including three light sources. Each of the light sources may be configured to emit light within a wavelength range corresponding to a wavelength range to which a photoreceptor cell may be responsive to. More specifically, the first light source may be configured to emit light having a wavelength range corresponding to a generally red color, corresponding to a wavelength range that long-type cone cells are responsive to, the second light source may emit light having a wavelength range corresponding to a generally green color, corresponding to a wavelength range that medium-type cone cells are responsive to, and the third light source may emit lighting having a wavelength range corresponding to a generally blue color, corresponding to a wavelength range that short-type cone cells are responsive to.

The method 900 may start at Block 910. At Block 920, the lighting device may operate the first light source to emit a first light for a first period. The first period may be within the operational period range as described hereinabove. The method may then continue at Block 930, where the lighting device may operate the second light source to emit a second light for a second period. The second period may similarly be within the operational period as described hereinabove. The method may then continue at Block 940, where the lighting device may operate the third light source to emit a third light for a third period. Again, the third period may be within the operational period as described hereinabove.

Moreover, each of the first period, the second period, and third period may be approximately equal, or they may be different, while still being within the operational period range. The lighting device may selectively vary the first, second, and third periods to alter the color of light perceived by the visual cortex, wherein the longer the period is, the perceived color appears to be more closely related to the color of light associated with the period. For example, if the first period is relatively longer than either of the second period and the third period, the combined light, as described hereinabove, will appear to be redder in color. Accordingly, the color of the combined light may be controlled according to the principles of additive colors, as known in the art.

The method may continue at Block 950, where the lighting device may determine whether to continue to emit light. This determination may be performed by the circuitry, which may include a controller, as described for the lamp 200 hereinabove. If it is determined that the lighting device will continue emitting light, then the method may continue by returning to Block 920. If, however, it is determined the lighting device will not continue emitting light, then the method may end at Block 960.

Figure 10:
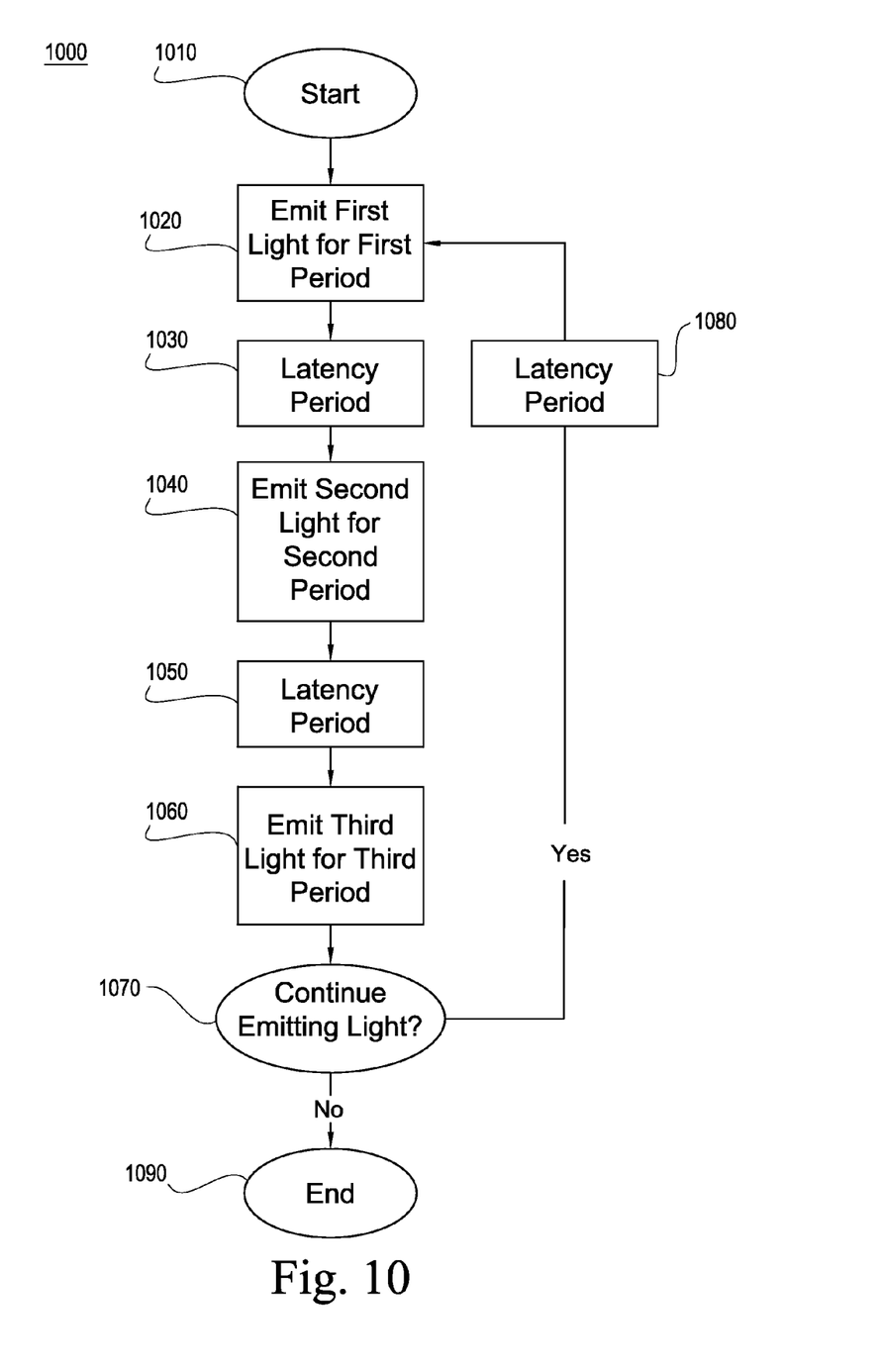
FIG. 10 is a flowchart illustrating a method of emitting light according to the embodiment of FIG. 9 further including a latency period.

Referring now to FIG. 10, a flowchart illustrating a method 1000 of operating a lighting device to emit light that reduces physioneural compression similar to the method presented in FIG. 9 is presented. In the method 1000 of FIG. 10, a lighting system may be configured to include a latency period between the subsequent emissions of light from light sources. The lighting system of the present embodiment may be similar to that of the embodiment presented in FIG. 9, wherein the lighting system may be a lighting device including three light sources. Each of the light sources may be configured to emit light within a wavelength range corresponding to a wavelength range to which a photoreceptor cell may be responsive to. More specifically, the first light source may be configured to emit light having a wavelength range corresponding to a generally red color, corresponding to a wavelength range that long-type cone cells are responsive to, the second light source may emit light having a wavelength range corresponding to a generally green color, corresponding to a wavelength range that medium-type cone cells are responsive to, and the third light source may emit lighting having a wavelength range corresponding to a generally blue color, corresponding to a wavelength range that short-type cone cells are responsive to. Moreover, the lighting system of the present embodiment may be configured to include a latency period between operation of each of the lighting devices, as described hereinabove, specifically in describing the embodiment presented in FIG. 8.

The method 1000 may start at Block 1010. At Block 1020, the lighting device may operate the first light source to emit a first light for a first period. The first period may be within the operational period range as described hereinabove. The method 1000 may then continue at Block 1030, where the lighting device may then enter a latency period during which the lighting device does not operate any light source of the lighting device, causing the lighting device to emit no light. The latency period may be characterized the same as the latency period presented in FIG. 8. The method 1000 may then continue at Block 1040, where the lighting device may operate the second light source to emit a second light for a second period. The method 1000 may continue at Block 1050, where the lighting device enters another latency period. The method 1000 may continue yet further at Block 1060, where the lighting device may operate the third light source to emit a third light for a third period. Each of the first, second, and third light periods may be of varying lengths, as described hereinabove.

The method 1000 may continue at Block 1070, where the lighting device may determine whether to continue to emit light. This determination may be performed by the circuitry, which may include a controller, as described for the lamp 200 hereinabove. If it is determined that the lighting device will continue emitting light, then the method 1000 may continue at Block 1080, where the lighting device may enter another latency period. The method 1000 may then return to Block 1020. If, however, it is determined at Block 1070 the lighting device will not continue emitting light, the method may end at Block 1090.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

What is claimed is:

1. A system for generating light with reduced physioneural compression comprising:
   a first light source operable to emit light within a first wavelength range corresponding to a first color;
   a second light source operable to emit light within a second wavelength range corresponding to a second color; and
   a controller functionally coupled to each of the first light source and the second light source;
   wherein the controller is configured to alternately operate each of the first and second light sources with a duty cycle within an operational period within the range from 2 milliseconds to 20 milliseconds; and
   wherein the controller is configured to include a latency period between operation of the first and second light sources.

2. A system according to claim 1 wherein the first light source and the second light source comprise a pair of opponent colors selected from the group consisting of a red and green opponent pair and a yellow and blue opponent pair.

3. A system according to claim 1 wherein the latency period is greater than or approximately equal to 50 nanoseconds.

4. A system according to claim 1 wherein the light emitted by the first light source and the second light source is perceivable by an observer as a combined light having a perceived brightness; and wherein the controller is configured to control the perceived brightness of the combined light by modifying an emission sequence of the first and second light sources.

5. A system according to claim 1 wherein the controller is configured to control the perceived brightness of the combined light by at least one of reducing the period of operation of at least one of the first light source and the second light source and increasing a latency period between operation of the first and second light sources.

6. A lighting system according to claim 1 wherein the perceived brightness of the system is approximately equal to:

$$B = \left(\left(\frac{1}{3}\right)^{-6} L^{0.6}\right)3,$$

where B is perceived brightness and L is luminance.

7. A system for generating light with reduced physioneural compression comprising:
   a first light source configured to emit light that generates a response primarily in long cone cells;
   a second light source configured to emit light that generates a response primarily in medium cone cells;
   a third light source configured to emit light that generates a response primarily in short cone cells; and
   a controller functionally coupled to each of the first light source, the second light source, and the third light source;
   wherein the controller is configured to alternately operate at least two of the first light source, the second light source, and the third light source;
   wherein the controller is configured to alternately operate the light sources to emit light for a period within an operational period within the range from 2 milliseconds to 20 milliseconds; and
   wherein the controller is configured to include a latency period between operation of at least two of the first light source, the second light source, and the third light source.

8. A system according to claim 7 wherein the latency period is greater than or approximately equal to a 50 nanoseconds.

9. A system according to claim 7 wherein the first light source is configured to emit light having a generally red color; wherein the second light source is configured to emit light having a generally green color; and wherein the third light source is configured to emit light having a generally blue color.

10. A system according to claim 9 wherein the controller is configured to alternately operate each of the first light source and the second light source to produce a combined light that is approximately purple in color; wherein the controller is configured to alternately operate each of the first light source and the third light source to generate a combined light that is approximately yellow in color; and wherein the controller is configured to alternately operate the second light source and the third light source to generate a combined light that is approximately light blue in color.

11. A system according to claim 9 wherein the controller is configured to sequentially operate the first light source, the second light source, and the third light source to generate a white light; and wherein the period operating the sequence of the first light source, followed by the second light source, followed by the third light source is within the operational period range.

12. A system according to claim 11 wherein the controller is configured to operate the first light source, the second light source, and the third light source for independently variable periods of time; wherein the controller is configured to operate at least one of the first light source and the second light source for a greater period of time than the third light source to generate a combined light having a color temperature less than about 6000 Kelvin; and wherein the controller is configured to operate the third light source for a greater period of time than the first light source to generate a combined light having a color temperature greater than about 6000 Kelvin.

13. A method of emitting light having reduced physioneural compression using a lighting system comprising a first light source configured to emit light that generates a response primarily in long cone cells, a second light source configured to emit light that generates a response primarily in medium cone cells, a third light source configured to emit light that generates a response primarily in short cone cells, and a controller functionally coupled to each of the first light source, the second light source, and the third light source, the method comprising the steps of:

operating one of the first light source, the second light source, and the third light source for a first period;

not operating either of the first light source and the second light source for a latency period between the first period and the second period; and operating one of the first light source, the second light source, and the third light source that is a color opponent of the light source operated during the first period for a second period;

wherein the time elapsed during the sum of the first period and the second period is less than 20 milliseconds; and wherein the time elapsed during each of the first period and the second period is greater than 2 milliseconds.

14. A method according to claim 13 wherein the time elapsed during the sum of the first period, the second period, and the latency period is less than 20 milliseconds; and wherein the time elapsed during each of the first period and the second period is greater than 2 milliseconds.

15. A method according to claim 13 wherein the latency period is greater than or approximately equal to 50 nanoseconds.

16. A method according to claim 13 further comprising the step of operating one of the first light source, the second light source, and the third light source that was not operated during either of the first period and the second period for a third period; wherein the time elapsed during the sum of the first period, the second period, and the third period is less than 20 milliseconds; and wherein each of the first period, the second period, and the third period is greater than 2 milliseconds.

17. A method according to claim 16 further comprising the steps of:

not operating any of the first light source, the second light source, and the third light source for a first latency period between the first period and the second period; and not operating any of the first light source, the second light source, and the third light source for a second latency period between the second period and the third period;

wherein the time elapsed during the sum of the first period, the second period, the third period, the first latency period, and the second latency period is less than 20 milliseconds; and wherein the first period, the second period, and the third period are each greater than 2 milliseconds.

18. A method according to claim 17 wherein each of the first latency period and the second latency period are greater than or approximately equal to 50 nanoseconds.

* * * * *